United States Patent [19]

Bujan et al.

[11] 4,335,717

[45] Jun. 22, 1982

[54] I.V. ADMINISTRATION SET WITH RETROGRADE VOLUME

[75] Inventors: Albert F. Bujan, Waukegan; Garfield A. Dawe, Lindenhurst, both of Ill.

[73] Assignee: Abbott Laboratories, North Chicago, Ill.

[21] Appl. No.: 195,899

[22] Filed: Oct. 10, 1980

[51] Int. Cl.³ .............................................. A61M 5/14
[52] U.S. Cl. ........................... 128/214 G; 128/214 C; 128/214 R; 128/214.2
[58] Field of Search ........... 128/214 G, 214 R, 214 F, 128/214 C, DIG. 12, 214.2

[56] References Cited

U.S. PATENT DOCUMENTS

| | | | |
|---|---|---|---|
| 2,188,507 | 1/1940 | Harris | 128/214 R |
| 2,825,492 | 3/1958 | Krasno | 128/214 R |
| 2,969,063 | 1/1961 | Broman | 128/214.2 |
| 3,650,023 | 3/1972 | Rosenberg | 55/159 |
| 3,677,242 | 7/1972 | Shaye | 128/214 C |
| 3,861,388 | 1/1975 | Vaugn | 128/214 R |
| 3,934,576 | 1/1976 | Danielsson | 128/214 R |
| 4,034,754 | 7/1977 | Viray | 128/214 R |
| 4,114,617 | 9/1978 | Gurner et al. | 128/214 R |
| 4,146,028 | 3/1979 | LeFevre | 128/227 |
| 4,200,095 | 4/1980 | Reti | 128/214 C |
| 4,278,084 | 7/1981 | Pope, Jr. | 128/214 R |

FOREIGN PATENT DOCUMENTS 1182016  2/1970  United Kingdom ........... 128/214 C

*Primary Examiner*—Lee S. Cohen
*Assistant Examiner*—Nancy A. B. Swisher
*Attorney, Agent, or Firm*—Robert L. Niblack; Neil E. Hamilton

[57] ABSTRACT

An I.V. administration set is provided with a flexible expansion section so as to accommodate an additional volume of liquid without the use of excessive lengths of tubing. The expansion section is in the form of pleated or corrugated tubing which, upon the introduction of liquid into an I.V. set such as by means of a hypodermic syringe, will accommodate an additional portion of liquid which is known in the I.V. administration art as a retrograde volume.

10 Claims, 4 Drawing Figures

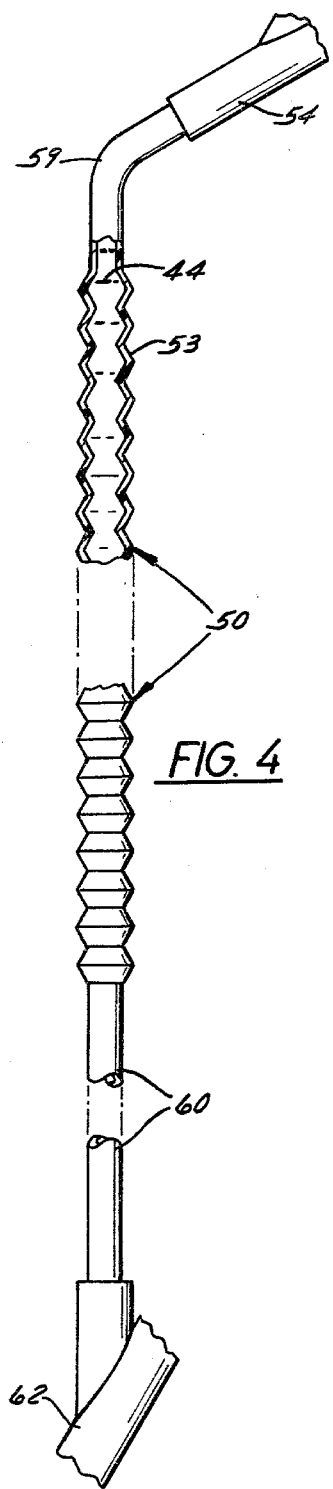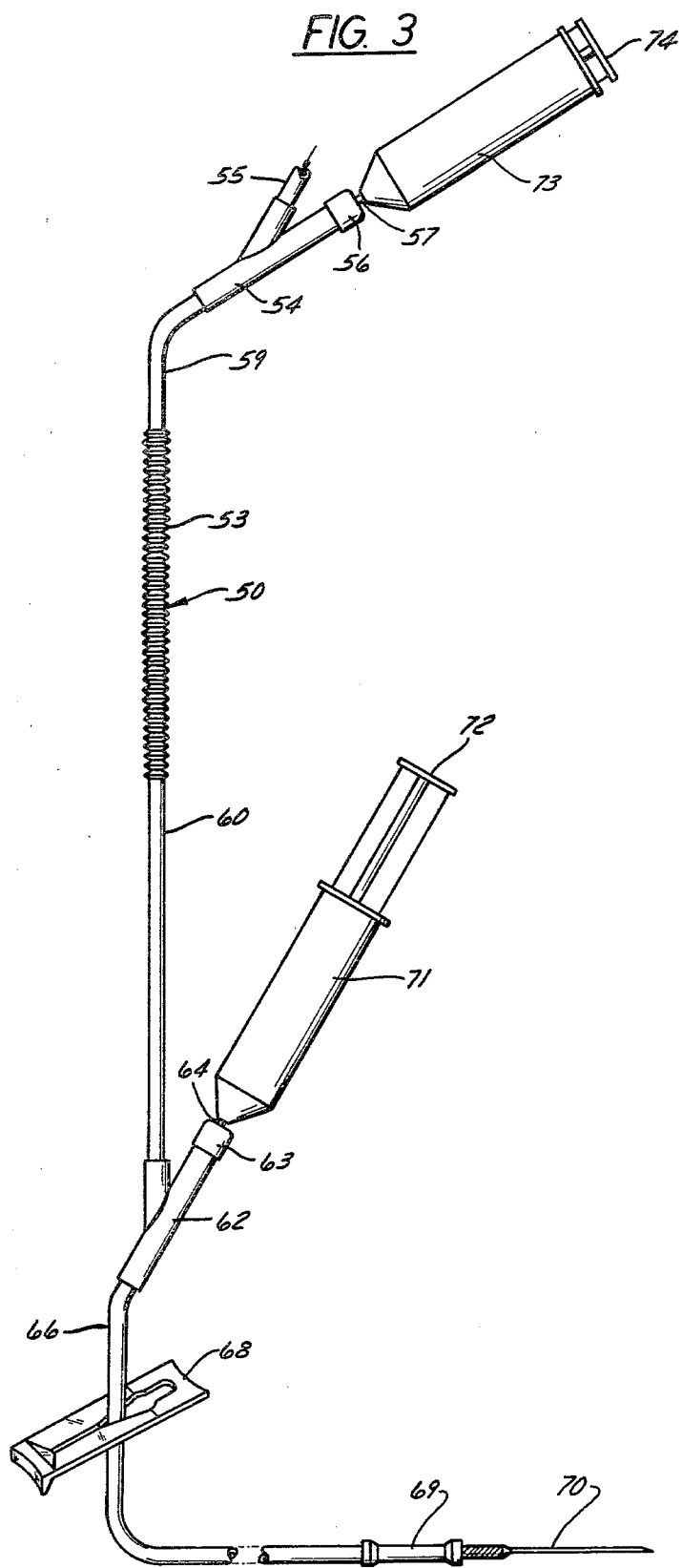

I.V. ADMINISTRATION SET WITH RETROGRADE VOLUME

BACKGROUND OF THE INVENTION

This invention relates to an I.V. adminsitration set which will accommodate retrograde volumes of liquid without requiring an excessive length of tubing. More particularly, this invention relates to the placement in an I.V. administration set of a fluid expansion means in the form of a pleated section of tubing or corrugated tubing, which, when placed between two injection sites for a hypodermic syringe, will accommodate a large volume of liquid.

During I.V. liquid administration, a new and useful procedure to administer additional medication is accomplished by providing two injection sites separated by a measured length of tubing which is designated as capable of holding a specific volume of liquid. The procedure involves the connecting of a syringe with medication to the lower injection site and an empty, depressed syringe, to the upper injection site. By injecting the medication with the syringe at the lower injection site, the prime fluid in the tubing is forced into the empty syringe, filling the tubing with medication. The syringes are then removed, and a clamp which was previously closed below the lower injection site is opened. The flow rate is then set by a suitable means such as a flow control clamp and the administration commences: the added medication entering first, followed by the primary liquid.

Nowhere in the prior art is there provided an I.V. administration set with an expandable member which is collapsible when empty, yet will permit the introduction of an extra volume of liquid, which as previously explained, is required where the use of retrograde volumes of liquid are administered.

It is an advantage of the present invention to provide an I.V. administration set which will permit the introduction of retrograde volume of liquid while obviating the use of an excessive length of tubing. Other advantages are an I.V. administration set with a retrograde volume feature which is compact and thus requiring a minimum amount of space for packaging; a retrograde feature for an I.V. administration set which is easily employed during administration procedures; and I.V. administration set with an expandable length of tubing which can be easily fabricated into an I.V. set without substantially increasing the cost thereof.

SUMMARY OF THE INVENTION

The foregoing advantages are accomplished and the shortcomings of the prior art are overcome by the present apparatus for administering a parenteral liquid wherein a liquid-type connection means communicates with the liquid in the container and is attached to a first length of flexible tubing. Means are provided to control the flow of liquid through the first length of flexible tubing and a sight drip chamber is also in fluid communication therewith. A first injection site is connected to said first length of tubing at one end and a second injection site is spaced from the first. A flexible expansion means is positioned between the first and second injection sites and in fluid communication therewith. A second length of flexible tubing communicates with the second injection site. Means are provided to interconnect the second length of tubing to a hypodermic needle opposite the second injection site. The flexible expansion means is preferably in the form of pleated, flexible tubing. In one form, the pleated tubing is provided by an outwardly pleated wall section and, in another form it is a length of corrugated tubing. The flexible expansion means provides space for a retrograde volume of liquid during I.V. administration. Accordingly, when a hypodermic syringe is positioned in the second injection site and the liquid therein forced into the tubing, the flexible expansion means will expand to accommodate a certain volume of retrograde liquid as will the hypodermic syringe which is placed in the first injection site. This procedure allows for a shorter length of tubing to be employed between the injection sites.

DESCRIPTION OF THE DRAWING

A better understanding of the present fluid expansion means for an I.V. administration set will be accomplished by reference to the drawing wherein:

FIG. 3 is a view in side elevation of an alternative embodiment shown with only a portion of the I.V. administration set.

FIG. 4 is a partial and enlarged view of FIG. 3 showing the flexible expansion means of FIG. 3 in an expanded state.

DESCRIPTION OF THE PREFERRED EMBODIMENT

Figure 1:
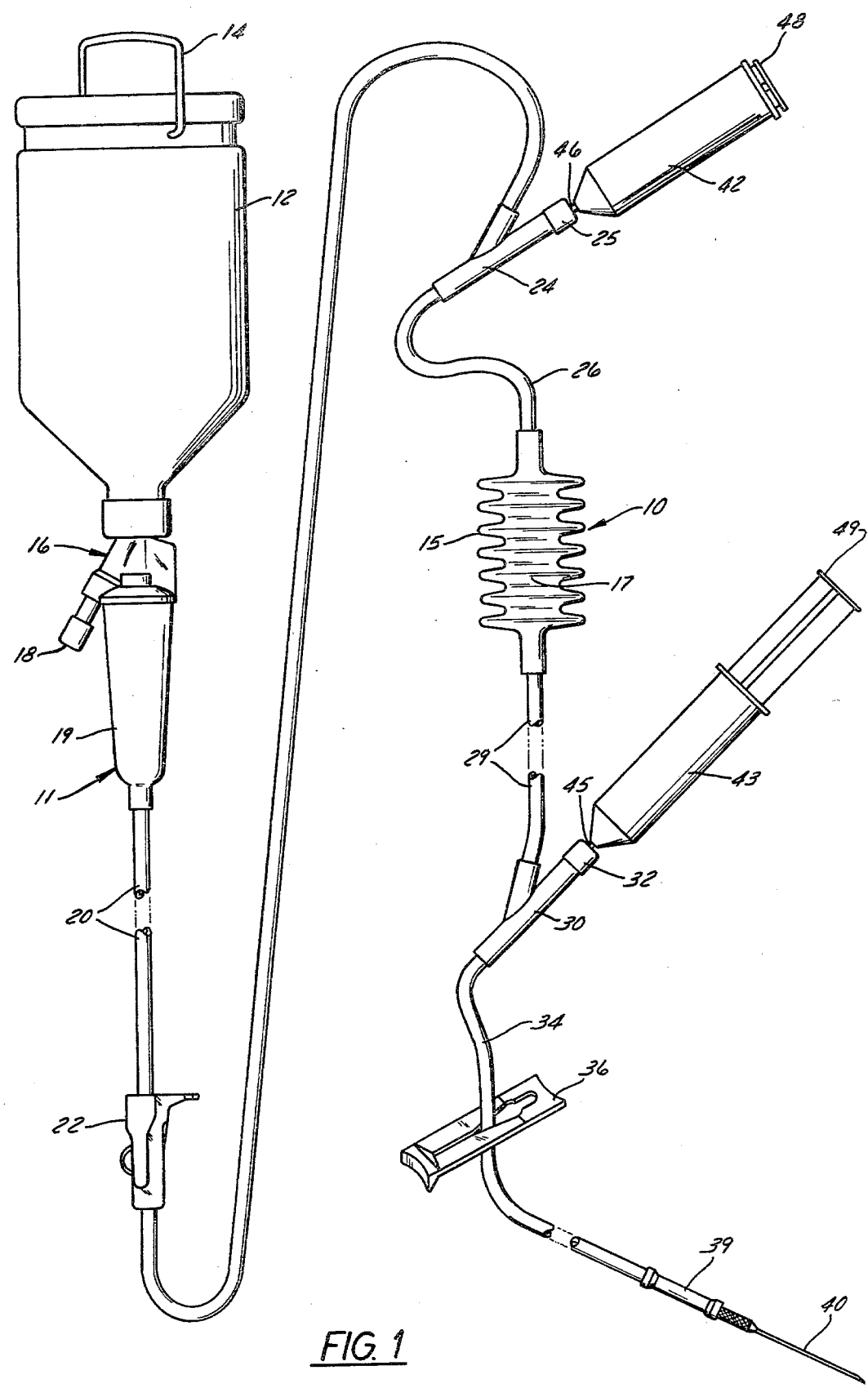
FIG. 1 is a view in side elevation of an I.V. administration set including the flexible expansion means prior to the introduction of a retrograde volume of liquid.

Proceeding to a detailed description of the present invention, the flexible expansion means, generally 10, is shown in FIG. 1 in conjunction with a standard I.V. set, generally 11, which will include two spaced apart injection sites 24 and 30 which are connected to the flexible expansion means, generally 10, by means of lengths of tubing 26 and 29. Flexible expansion means 10 is composed of an outwardly pleated, flexible tubing having expandable wall sections 15 and a central passageway 17 having a width greater than the diameter of tubing 26 and 29. The I.V. administration set 11 will include the usual I.V. solution container 12 which will be supported by the usual support means through bail 14. A vented piercing pin, generally 16, will have the usual drip chamber 19 and air vent 18. A length of tubing 20 will interconnect drip chamber 19 with Y-injection site 24 and the flow of liquid through tubing 20 is controlled by a flow control clamp 22. At the opposite end of the set is a length of tubing 34 connected with Y-injection site 30 and the flow of liquid therethrough controlled by slide clamp 36. A needle adapter 39 provides attachment for hypodermic needle 40. Two hypodermic syringes 42 and 43 having hypodermic needles 46 and 45, respectively, are placed in pierceable engagement with reseal caps 25 and 32 of Y-injection sites 24 and 30, respectively.

Figure 2:
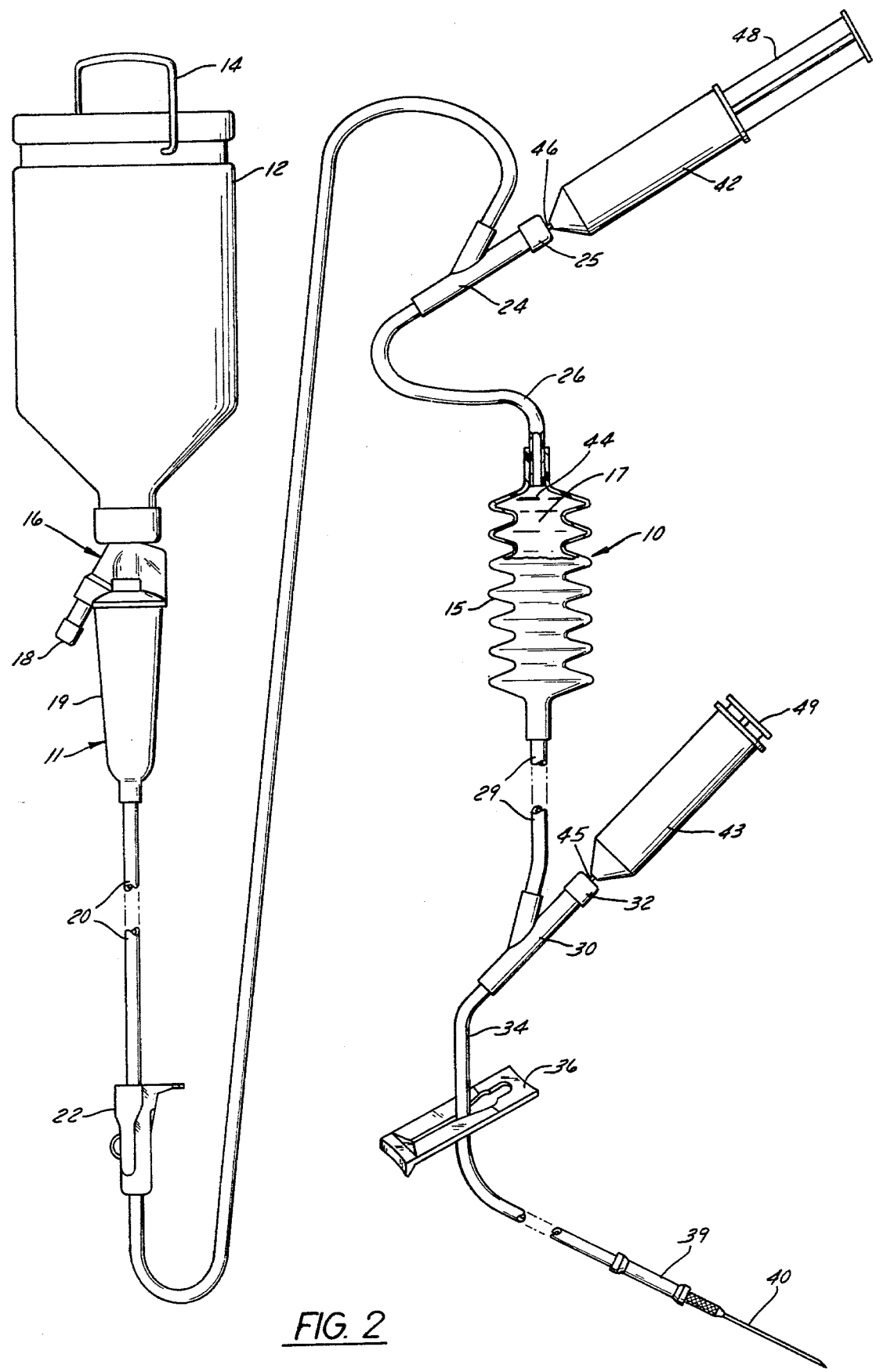
FIG. 2 is a view similar to FIG. 1 of the I.V. set shown therein and illustrating the flexible expansion means in an expanded position.

FIG. 2 illustrates the flexible expansion means 10 when it will be filled with a retrograde volume of fluid 44 supplied by syringe 43. It will be noted that the fluid 44 fills the space between the pleated wall sections 15. This will be explained later in the operation.

FIG. 3 illustrates an alternative embodiment, generally 50, of a flexible expansion means wherein the flexible expansion means is in the form of a length of corrugated tubing having pleated side walls 53. As is similar to flexible expansion means 10, it is utilized in the same I.V. administration set as illustrated in FIG. 1, with a length of tubing 55 interconnected to drip chamber 19 and solution container 12 as well as to first injection site 54. Tubing 59 is also interconnected with injection site 54 having a reseal cap 56 for engagement with hypodermic syringe 73 by means of needle 57. A length of tubing 60 also connects corrugated tubing 50 with a second injection site 62 which communicates with hypodermic syringe 71 by means of needle 64 passing through reseal cap 63. Another length of tubing 66 extends from reseal site 62 with the flow therethrough controlled by slide clamp 68. Needle adapter 69 secures hypodermic needle 70 thereto.

FIG. 4 is an enlarged view showing the corrugated tubing 50 with side walls 53 in the expanded state and the retrograde fluid 44 contained therein. This will be later referred to in the operation immediately to follow.

OPERATION

A better understanding of the advantages of the flexible expansion means 10 and 50 will be had by reference to their operation.

The I.V. administration set 11 will be packaged in the usual manner as illustrated in FIG. 1 except that the hypodermic syringes 42 and 43 will not be in contact with the injection sites 24 and 30. Neither is the hypodermic needle 40 nor I.V. solution container 12 usually attached. When it is desired to administer the fluid in container 12, the hypodermic needle 40 will be attached to needle adapter 39 and the vented piercing pin and drip chamber 16 pierced through the usual rubber stopper in container 12. Fluid flow will be controlled through the set by means of flow control clamp 22 and by opening slide clamp 36. When it is desired to administer the retrograde additive liquid in syringe 43, such as vitamins, the slide clamp 36 will be placed in a closed position and hypodermic syringe 42 will be positioned in contact with Y-injection site 24 with hypodermic needle 46 pierced through reseal cap 25 and plunger 48 in an inward position. When it is desired to introduce the additive material, syringe 43 will have hypodermic needle 45 pierced through cap 32 and the contents of the syringe delivered into the Y-reseal injection site 30 by moving plunger 49 into the syringe barrel. As clamp 36 is in a closed position, the contents of the syringe will fill into tubing 34 and 29 whereupon it will expand into the expansion means 10. As this is occurring, the liquid in the expansion means 10 will in many instances fill it completely until it appears in the condition shown in FIG. 2. The excess liquid will then flow into tubing 26 and syringe 42 with an automatic moving outwardly of plunger 48. It will be recognized also that tubing clamp 22 will be in a position to close tubing 20 which will have previously been filled with liquid from container 12. To deliver the retrograde volume of liquid 44, all that is required is that the syringes be removed from the injection sites and slide clamp 36 be opened. The retrograde volume will flow out to hypodermic needle 40 until the expansion means will assume the previous condition as indicated in FIG. 1.

The operation of the expansion member 50 shown in FIGS. 3 and 4 will be as previously described for unit 10. Pleated tubing 53 will be in a collapsed condition before the retrograde fluid is introduced which is illustrated in FIG. 3. With the retrograde fluid 44 introduced it will assume a position as shown in FIG. 4. Accordingly, the only difference between utilizing the corrugated tubing 50 over the pleated chamber 10 is that it will be effected over a longer vertical dimension.

The pleated or corrugated tubing representing the flexible expansion means 10 and 50 is composed of a resinous, plastic material such as polyvinyl chloride and can be formed in the usual manner into the pleated or corrugated condition. It is assembled in an I.V. set such as between two lengths of tubing 26 and 29 by solvent bonding as the same plastic material can be used for the tubing as well as for the expansion means 10 or 50. Alternatively, different thermoplastic materials can be used such as polyolefins and still be sealed or bonded together such as by means of epoxies.

It will be appreciated that in place of a vented piercing pin 16 a nonvented one could be employed when a self collapsing container is employed such as a flexible container. Further, when the flexible expansion means 10 or 50 is employed with a positive pressure system, such as an I.V. pump, it is important that the expandable wall sections 15 and 53 remain in one of two stable conditions, extended or collapsed. If they are allowed to collapse by their own resilience, they will influence the delivery rate and may bolus the patient. The preferred manner is to have them extended until the medication has been pushed toward the patient. They could then be collapsed by compressing them to their original shape. They would then be ready for use for the next retrograde medication procedure. It is apparent that some means of holding the expansion sections extended or collapsed against the pump pressures (up to 40 psi) must be employed if they are to be utilized in conjunction with an I.V. pump. This would be accomplished in using materials and fabrication methods to adjust the force required to expand or contract the pleated walls. The expansion or contracting sections should be of such rigidity that the sections, when filled with medication, will remain extended. Controlled expansion is also required for if they expand unintentionally, the unit can draw blood into the catheter or needle.

Upper injection sites 24 and 54 are disclosed in conjunction with flexible expansion means 10 and 50. While resulting in a less practical unit, these could be eliminated if the additive volume is less than the volume of the expanded section and the clamps above and below are closed when filling. Overfilling will pressurize the capacity between the clamps: if the upper clamp is opened first, excess will go up to the drip chamber; if the lower clamp is opened, the excess will be delivered to the patient (bolus). In utilizing the two syringe systems, one should be aware not to remove the same amount as added.

It will thus be seen that through the present invention there is now provided a flexible expansion member for an I.V. administration set which will allow for varying the retrograde volume of an additive I.V. fluid. The flexible expansion member permits a large volume of liquid to be placed in an I.V. administration set between the respective injection sites obviating the need for a long length of flexible tubing. As will be readily appreciated, the I.V. solution container is usually set at a predetermined distance above the patient and the use of a long length of flexible tubing can be a problem because of potential kinking or constriction. It will be further seen that the flexible expansion means is simple in its construction and can be readily fabricated from standard thermoplastic materials and molding techniques.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

We claim:

1. A liquid dispensing apparatus for administering a parenteral liquid from a container to a recipient comprising:
    a liquid-tight connection means for communicating with said liquid from a container;
    a first length of flexible tubing secured to said connection means at one end;
    means to control the flow rate of liquid through said first length of flexible tubing;
    a sight-drip chamber in fluid communication with said first length of flexible tubing and said connection means;
    a first injection site in fluid communication with said first length of flexible tubing at the other end thereof;
    a second injection site in fluid communication with said first length of flexible tubing and spaced from said first injection site;
    flexible expansion means for accomodating an additional volume of liquid, positioned between said first and second injection sites and in fluid communication therewith;
    a second length of flexible tubing in fluid communication with said second injection site; and
    means to interconnect a hypodermic needle to said second length of tubing opposite said second injection site.

2. The apparatus for administering a parenteral liquid as defined in claim 1 wherein said flexible expansion means is defined by pleated, flexible tubing.

3. The apparatus for administering a parenteral liquid as defined in claim 2 wherein said flexible expansion means is joined to said first and second injection site by means of additional lengths of tubing and the central passageway through said expansion means has a width greater than the diameter of said additional lengths of tubing.

4. The apparatus for administering a parenteral liquid as defined in claim 2 wherein said flexible expansion means is defined by an outwardly pleated wall section with said section constructed and arranged to receive said additional liquid.

5. The apparatus for administering a parenteral liquid as defined in claim 2 wherein said liquid tight connection means comprises an air vented piercing pin assembly with said sight-drip chamber secured to said pin assembly.

6. The apparatus for administering a parenteral liquid as defined in claim 1 wherein said flexible expansion means is defined by a length of corrugated tubing.

7. The apparatus for administering a parenteral liquid as defined in claim 1 wherein said flow control means is defined by a tubing clamp.

8. The apparatus for administering a parenteral liquid as defined in claim 1 wherein said first and second injection sites are defined by a Y-type adapter with a reseal plug.

9. The apparatus for administering a parenteral liquid as defined in claim 1 further including shut-off means operatively associated with said second length of tubing.

10. The apparatus for administering a parenteral liquid as defined in claim 1 wherein said means to interconnect a hypodermic needle to said second length of tubing is a needle adapter.

* * * * *